United States Patent [19]
Oxman et al.

[11] Patent Number: 6,025,406
[45] Date of Patent: Feb. 15, 2000

[54] TERNARY PHOTOINITIATOR SYSTEM FOR CURING OF EPOXY RESINS

[75] Inventors: Joel D. Oxman, St. Louis Park, Minn.; Dwight W. Jacobs, Hudson, Wis.

[73] Assignee: 3M Innovative Properties Company, St. Paul, Minn.

[21] Appl. No.: 08/838,835

[22] Filed: Apr. 11, 1997

[51] Int. Cl.[7] ............................... C08F 2/50; A61K 6/08; C08G 65/04

[52] U.S. Cl. ................... 522/14; 522/15; 522/25; 522/170; 522/908; 523/116; 528/307; 528/406; 528/421; 528/408

[58] Field of Search .................. 522/15, 25, 31, 522/39, 48, 100, 103, 170, 14, 908; 523/116; 528/307, 406, 408, 421

[56] References Cited

U.S. PATENT DOCUMENTS

| | | | |
|---|---|---|---|
| 3,018,262 | 1/1962 | Schroeder | 260/29.2 |
| 3,117,099 | 1/1964 | Proops | 260/18 |
| 3,729,313 | 4/1973 | Smith | 96/27 |
| 3,741,769 | 6/1973 | Smith | 96/35.1 |
| 3,808,006 | 4/1974 | Smith | 96/88 |
| 4,250,053 | 2/1981 | Smith | 252/426 |
| 4,256,828 | 3/1981 | Smith | 430/280 |
| 4,394,403 | 7/1983 | Smith | 427/42 |
| 4,503,169 | 3/1985 | Randklev | 523/117 |
| 4,642,126 | 2/1987 | Zador | 51/295 |
| 4,652,274 | 3/1987 | Boettcher | 51/298 |
| 4,695,251 | 9/1987 | Randklev | 433/8 |
| 4,735,632 | 4/1988 | Oxman et al. | 522/14 |
| 4,828,583 | 5/1989 | Oxman et al. | 522/14 |
| 4,835,193 | 5/1989 | Hayase | 522/15 |
| 5,545,676 | 8/1996 | Palazzotto | 522/15 |

FOREIGN PATENT DOCUMENTS

| | | |
|---|---|---|
| WO 95/14716 | 6/1995 | WIPO . |
| WO 96/13538 | 5/1996 | WIPO . |

OTHER PUBLICATIONS

Beringer et al., J. Am. Chem. Soc. 81,342 (1959).

*Primary Examiner*—Susan W. Berman
*Attorney, Agent, or Firm*—Dale A. Bjorkman

[57] ABSTRACT

Photocurable, addition polymerizable compositions contain an epoxy resin and a photoinitiator system containing (a) an epoxy resin and (b) a photoinitiator system comprising: (i) an iodonium salt; (ii) a visible light sensitizer; and (iii) an electron donor compound, wherein the photoinitiator system has a photoinduced potential of at least about 0 mV relative to a standard solution of $2.9 \times 10^{-5}$ moles/g diphenyl iodonium hexafluoroantimonate and $1.5 \times 10^{-5}$ moles/g camphorquinone in 2-butanone. The compositions cure on exposure to light in the visible spectrum and are useful in a variety of applications, including dental adhesives and composites.

31 Claims, No Drawings

TERNARY PHOTOINITIATOR SYSTEM FOR CURING OF EPOXY RESINS

FIELD OF THE INVENTION

The invention relates to photocurable, addition polymerizable compositions that contain a ternary photoinitiator system that is activated on exposure to actinic radiation in the visible spectrum and methods of curing addition polymerizable compositions using the photoinitiator system. The invention is additionally directed to methods of curing addition polymerizable compositions using the ternary photoinitiator system.

BACKGROUND OF THE INVENTION

Epoxy containing compounds are known to be curable using various cationic initiator systems. Smith, in U.S. Pat. No. 4,256,828, describes photopolymerizable compositions that contain epoxides, an organic compound with hydroxyl functionality, and a photosensitive aromatic sulfonium or iodonium salt of a halogen containing complex ion. Hayase et al., U.S. Pat. No. 4,835,193, describes photopolymerizable epoxy resin compositions that comprise an epoxy resin and a heteropoly-acid aromatic sulfonium salt as the photocuring catalyst. In WO 95/14716 Neckers et al. describe photohardenable compositions that comprise a cationically polymerizable compound, a xanthene or fluorone dye, a hydrogen donor, and an onium salt. Palazzotto et al., U.S. Pat. No. 5,545,676, describes addition polymerization of free-radically polymerizable materials. The photoinitiator system described in that patent comprises an aryliodonium salt, a sensitizer, and an electron donor having an oxidation potential less than or equal to that of p-dimethoxybenzene.

PCT published application No. WO 96/13538 describes a system for curing epoxy compounds by exposure to visible light by use of a system comprising an aryliodonium salt and a sensitizer. Comparative Example 34 of this disclosure describes the use of one of the initiator systems of Palazzotto et al., U.S. Pat. No. 5,545,676 in an epoxy/polyol resin system. N,N-dimethylbenzylamine is used as the electron donor. The results of this experiment indicated that the use of this amine donor tended to retard the cure of the resin system.

Suppliers of cationically cured resins expressly warn against using organic amines in photoinitiated epoxy resins. An example of such a warning is found in Union Carbide literature regarding Cyracure® cycloaliphatic epoxides.

SUMMARY OF THE INVENTION

We have discovered, and the invention provides, a photopolymerizable composition that contains an epoxy resin and a photoinitiator system containing an iodonium salt, a visible light sensitizer, and an electron donor compound, wherein the photoinitiator system has a photoinduced potential greater than or equal to that of 3-dimethylamino benzoic acid in a standard solution of $2.9 \times 10^{-5}$ moles/g diphenyl iodonium hexafluoroantimonate and $1.5 \times 10^{-5}$ moles/g camphorquinone in 2-butanone. Generally, 3-dimethylamino benzoic acid in this standard exhibits a photoinduced potential of at least about 115 mV relative to a standard solution of $2.9 \times 10^{-5}$ moles/g diphenyl iodonium hexafluoroantimonate and $1.5 \times 10^{-5}$ moles/g camphorquinone in 2-butanone.

These compositions are curable on exposure to light having a wavelength of about 400 to 1000 nm, and the invention provides a method of addition photopolymerization comprising the step of irradiating a photopolymerizable composition with light having a wavelength of about 400 to 1000 nm until the composition gels or hardens, the composition comprising an epoxy resin and a photoinitiator system containing an iodonium salt, a visible light sensitizer, and an electron donor compound wherein the photoinitiator system has a photoinduced potential of at least about 100 mV relative to a standard solution of $2.9 \times 10^{-5}$ moles/g diphenyl iodonium hexafluoroantimonate and $1.5 \times 10^{-5}$ moles/g camphorquinone in 2-butanone or has a photoinduced potential greater than or equal to that of 3-dimethylamino benzoic acid in a standard solution of $2.9 \times 10^{-5}$ moles/g diphenyl iodonium hexafluoroantimonate and $1.5 \times 10^{-5}$ moles/g camphorquinone in 2-butanone.

The initiator systems of the invention allow efficient cationic polymerization under conditions of room temperature and standard pressure. In addition, the initiator systems can, under appropriate conditions, initiate both cationic and free-radical polymerization. This property permits their use with a variety of photopolymerizable compositions. The use of these initiator systems actually results in the ability to cure epoxy systems otherwise not readily curable at room temperature with sensitizers and iodonium salts.

DETAILED DESCRIPTION OF THE INVENTION

The photopolymerizable compositions of the invention are sensitive throughout the visible spectral region and photocure without appreciable application of heat. The term "visible light" is used throughout this application to refer to light having a wavelength of about 400 to 1000 nanometers (nm). Photopolymerization of the compositions takes place on exposure of the compositions to a source of actinic radiation having a wavelength within this spectral region.

The cationically polymerizable epoxy resins useful in the compositions of the invention are organic compounds having an oxirane ring, i.e., a group of the formula

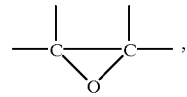

which is polymerizable by ring opening. Such materials, broadly called epoxides, include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. For example, the backbone may be of any type and substituent groups thereon can be any group that does not substantially interfere with cationic cure at room temperature. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexene oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to the U.S. Pat. No. 3,117,099, which is incorporated herein by reference.

Further epoxy-containing materials which are useful in the compositions of this invention include glycidyl ether monomers of the formula

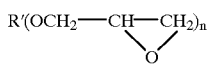

where R' is alkyl or aryl and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type are described in U.S. Pat. No. 3,018,262, which is incorporated herein by reference, and in "Handbook of Epoxy Resins" by Lee and Neville, McGraw-Hill Book Co., New York (1967).

There are a host of commercially available epoxy resins which can be used in this invention. In particular, epoxides which are readily available include octadecylene oxide, epichlorohydrin, styrene oxide, vinyl cyclohexene oxide, glycidol, glycidylmethacrylate, diglycidyl ether of Bisphenol A (e.g., those available under the trade designations "Epon 828", "Epon 825", "Epon 1004" and "Epon 1010" from Shell Chemical Co., "DER-33 1", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "CYRACURE UVR 6110" or UVR 6105" from Union Carbide Corp.), 3,4-epoxy-6-methylcyclohexylmethyl-3,4-epoxy-6-methylcyclohexene carboxylate (e.g., "ERL-4201" from Union Carbide Corp.), bis(3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp.), aliphatic epoxy modified from polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from -Dow Chemical Co.), 1,4-butanediol diglycidyl ether of phenolformaldehyde novolak (e.g., "DEN-43 1" and "DEN-438" from Dow Chemical Co.), and resorcinol diglycidyl ether (e.g., "Kopoxite" from Koppers Company, Inc.), bis(3,4-epoxycyclohexyl)adipate (e.g., "ERL-4299" or "UVR-6128", from Union Carbide Corp.), 2-(3,4-epoxycyclohexyl-5, 5-spiro-3,4-epoxy) cyclohexane-metadioxane (e.g., "ERL-4234" from Union Carbide Corp.), vinylcyclohexene monoxide 1,2-epoxyhexadecane (e.g., "UVR-6216" from Union Carbide Corp.), alkyl glycidyl ethers such as alkyl $C_8$–$C_{10}$ glycidyl ether (e.g., "HELOXY Modifier 7" from Shell Chemical Co.), alkyl $C_{12}$–$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-ter butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1 138" or "GY-281" from Ciba-Geigy Corp.), 9,9-bis[4-(2,3-epoxypropoxy)-phenyl]fluorenone (e.g., "Epon 1079" from Shell Chemical Co.).

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins are well known and contain such epoxides as epichlorohydrins, alkylene oxides, e.g., propylene oxide, styrene oxide; alkenyl oxides, e.g., butadiene oxide; glycidyl esters, e.g., ethyl glycidate.

The polymers of the epoxy resin may optionally contain other functionalities that do not substantially interfere with cationic cure at room temperature.

Blends of various epoxy-containing materials are also contemplated in this invention. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar. Other cationically polymerizable polymers may additionally be incorporated, if desired.

If desired, the composition can also contain a free-radically polymerizable material, including ethylenically unsaturated monomer, monomers or oligomers or polymers. Suitable materials contain at least one ethylenically unsaturated bond, and are capable of undergoing addition polymerization. Such free radically polymerizable materials include mono-, di- or poly- acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200–500, copolymerizable mixtures of acrylated monomers such as those in U.S. Pat. No. 4,652, 274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

If desired, the polymerizable material(s) may contain both epoxy and free-radically polymerizable functionalities in a single molecule. These may be obtained by reacting a di- or poly-epoxide with one or more equivalents of an ethylenically unsaturated carboxylic acid. Examples of such materials include the reaction product of VR-6105 (available from Union Carbide) or DER 332 with one equivalent of methacrylic acid. Commercially available materials having epoxy and free-radically polymerizable functionalities include the "Cyclomer" series, such as Cyclomer M100 or M101, available from Daicel Chemical, Japan.

The epoxy resin and optional free radically polymerizable material(s) are combined with a three component or ternary photoinitiator system. Three component initiator systems are described in Palazzotto et al., U.S. Pat. No. 5,545,676, which is incorporated herein by reference. The first component in the photoinitiator system is an iodonium salt, i.e., a diaryliodonium salt. The iodonium salt should be soluble in the monomer and preferably is shelf-stable, meaning it does not spontaneously promote polymerization when dissolved therein in the presence of the sensitizer and donor. Accordingly, selection of a particular iodonium salt may depend to some extent upon the particular monomer, sensitizer and donor chosen. Suitable iodonium salts are described in U.S. Pat. Nos. 3,729,313, 3,741,769, 3,808,006, 4,250,053 and 4,394,403, the iodonium salt disclosures of which are incorporated herein by reference. The iodonium salt can be a simple salt, containing an anion such as $Cl^-$, $Br^-$, $I^-$ or $C_4H_5SO_3^-$; or a metal complex salt containing an antimonate, arsenate, phosphate or borate such as $SbF_5OH^-$ or $AsF_6^-$. Mixtures of iodonium salts can be used if desired.

Examples of useful aromatic iodonium complex salt photoinitiators include: diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl) iodonium hexafluorophosphate; di(4-chlorophenyl) iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl) iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate.

Of the aromatic iodonium complex salts which are suitable for use in the compositions of the invention diaryliodonium hexafluorophosphate and diaryliodonium hexafluoroantimonate are among the preferred salts. These salts are preferred because, in general, they promote faster reaction, and are more soluble in inert organic solvents than are other aromatic iodonium salts of complex ions.

The aromatic iodonium complex salts may be prepared by metathesis of corresponding aromatic iodonium simple salts (such as, for example, diphenyliodonium bisulfate) in accordance with the teachings of Beringer et al., *J. Am. Chem. Soc.* 81,342 (1959). Thus, for example, the complex salt diphenyliodonium tetrafluoroborate is prepared by the addition at 60° C. of an aqueous solution containing 29.2 g silver fluoroborate, 2 g fluoroboric acid, and 0.5 g phosphorous acid in about 30 ml of water to a solution of 44 g (139 millimoles) of diphenyliodonium chloride. The silver halide that precipitates is filtered off and the filtrate concentrated to yield diphenyliodonium fluoroborate which may be purified by recrystallization.

The aromatic iodonium simple salts may be prepared in accordance with Beringer et al., above, by various methods including (1) coupling of two aromatic compounds with iodyl sulfate in sulfuric acid, (2) coupling of two aromatic compounds with an iodate in acetic acid-acetic anhydride-sulfuric acid, (3) coupling of two aromatic compounds with an iodine acrylate in the presence of an acid, and (4) condensation of an iodoso compound, an iodoso diacetate, or an iodoxy compound with another aromatic compound in the presence of an acid. Diphenyliodonium bisulfate is prepared by method (3), for example, by the addition over a period of eight hours at below 5° C. of a mixture of 35 ml of conc. sulfuric acid and 50 ml of acetic anhydride to a well-stirred mixture of 55.5 ml of benzene, 50 ml of acetic anhydride, and 53.5g of potassium iodate. The mixture is stirred for an additional four hours at 0–5° C. and at room temperature (about 25° C.) for 48 hours and treated with 300 ml of diethyl ether. On concentration, crude diphenyliodonium bisulfate precipitates and may be purified by recrystallization if desired.

The second component in the photoinitiator system is the sensitizer. The sensitizer should be soluble in the photopolymerizable composition, free of functionalities that would substantially interfere with the cationic curing process, and capable of light absorption somewhere within the range of wavelengths between about 300 and about 1000 nanometers.

Suitable sensitizers are believed to include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring deep cure (e.g., cure of highly-filled composites), it is preferred to employ sensitizers having an extinction coefficient below about 1000 $lmole^{-1}$ $cm^{-1}$, more preferably about or below 100 $lmole^{-1}$ $cm^{-1}$, at the desired wavelength of irradiation for photopolymerization. The alpha-diketones are an example of a class of sensitizers having this property, and are particularly preferred for dental applications By way of example, a preferred class of ketone sensitizers has the formula:

ACO(X)$_b$B where X is CO or CR$^1$R$^2$ where R$^1$ and R$^2$ can be the same different, and can be hydrogen, alkyl, alkaryl or aralkyl, b is zero, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable 1-diketones (b=1 and x=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'- 3 3'- and 4,4'-dihydroxylbenzil, furil, di-3,3'-indolylethanedione, 2,3-b omanedione (camphorquinone), biacetyl, 1,2-cyclohexanedione, 1,2-naphthaquinone, acenaphthaquinone, and the like.

Examples of particularly preferred visible light sensitizers include camphorquinone; glyoxal; biacetyl; 3,3,6,6-tetramethylcyclohexanedione; 3,3,7,7-tetramethyl-1,2-cycloheptanedione; 3,3,8,8-tetramethyl- 1,2-cyclooctanedione; 3,3,18,18-tetramethyl-1,2-cyclooctadecanedione; dipivaloyl; benzil; furil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; and 1,2-cyclohexanedione. Of these, camphorquinone is the most highly preferred sensitizer.

The third component of the initiator system is an electron donor. The electron donor compound(s) should meet one of the requirements set forth below and should be soluble in the polymerizable composition. The donor can also be selected in consideration of other factors, such as shelf stability and the nature of the polymerizable materials, iodonium salt and sensitizer chosen. A class of donor compounds that may be useful in the inventive systems may be selected from some of the donors described in Palazzotto et al., U.S. Pat. No. 5,545,676. Possible donor compounds that meet the criteria set forth by Palazzotto et al. must then be tested using one or both of the methods set forth below to determine if they will be useful donors for the photopolymerizable compositions of the invention.

The donor is typically an alkyl aromatic polyether or an alkyl, aryl amino compound wherein the aryl group is substituted by one or more electron withdrawing groups. Examples of suitable electron withdrawing groups include carboxylic acid, carboxylic acid ester, ketone, aldehyde, sulfonic acid, sulfonate and nitrile groups.

The suitability of a compound for usefulness in the compositions of the invention may be determined by measuring the photoinduced potential of a sample photoinitiator system that includes the compound. The photoinduced potential can be evaluated using one of two methods. In the first, a standard solution is prepared that contains 2.9×10$^{-5}$ moles/g of diphenyl iodonium hexafluoroantimonate and 1.5×10$^{-5}$ moles/g of camphorquinone in 2-butanone. A pH electrode is then immersed in the solution and a pH meter is calibrated to zero mV. A test solution of the standard solution and the compound is prepared next using the compound at a concentration of 2.9×10$^{-5}$ moles/g. This test solution is irradiated using blue light having a wavelength of about 400 to 500 nm having an intensity of about 200 to 400 mW/cm$^2$ for about 5 to 10 seconds. Millivolts relative to the standard solution are then determined by immersing the pH electrode in the test solution and obtaining a mV reading on the pH meter. For this method, useful donors are those compounds that provide a reading of at least 100 mV relative to the standard solution and provide a gel time for the compositions that fail to gel at 25 C in the absence of donor. Higher mV readings are generally indicative of greater activity, and to obtain a more rapid cure reading of at least about 100 mV are preferred.

In some instances there may be some uncertainty regarding the outcome of the above procedure. This may be due to questions or uncertainty arising from the instrumentation employed, from the way the procedure was carried out, or other factors, or one may wish to verify the suitability of a particular compound. A second test may be performed to verify the result obtained by following the above procedure and resolve any such uncertainty.

The second method involves the evaluation of the photoinduced potential of an initiator system that includes the compound compared to a system that includes 3-dimethylamino benzoic acid. For this method, a standard solution of 2.9×10$^{-5}$ moles/g diphenyl iodonium hexafluoroantimonate, 1.5×10$^{-5}$ moles/g camphorquinone and 2.9×10$^{-5}$ moles/g of 3-dimethylamino benzoic acid in 2-butanone is prepared. A pH electrode is then immersed in the solution and a pH meter is calibrated to zero mV. The standard solution is irradiated with blue light having a wavelength of between about 400–500 nm and an intensity of about 200 to 400 mW/cm$^2$ for about 5 to 10 seconds using a focused light source such as a dental curing light. After light exposure, the potential of the solution is measured by immersing a pH electrode in the irradiated standard solution and reading the potential in mV using a pH meter. A test solution is then prepared using 2.9×10$^{-5}$ moles/g of diphenyl iodonium hexafluoroantimonate, 1.5×10$^{-5}$ moles/g of camphorquinone and 2.9×10$^{-5}$ moles/g of the compound in 2-butanone. The test solution is irradiated and the photoinduced potential measured using the same technique as described for the standard solution. If the test solution has a photoinduced potential that is the same as or greater than that of the 3-dimethylamino benzoic acid containing standard solution, then the compound is a useful donor.

A preferred group of alkyl, aryl amine donor compounds is described by the following structural formula:

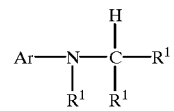

wherein R$^1$ are independently H; C$_{1-18}$ alkyl that is optionally substituted by one or more halogen, —CN, —OH, —SH, C$_{1-18}$ alkoxy, C$_{1-18}$ alkylthio, C$_{3-18}$ cycloalkyl, aryl, —COOH, —COOC$_{1-18}$ alkyl, —(C$_{1-18}$ alkyl)$_{0-1}$—CO—C$_{1-18}$ alkyl, or SO$_3$R$^2$; aryl that is optionally substituted by one or more electron withdrawing groups where R$^2$ is H; C$_{1-18}$ alkyl that is optionally substituted by one or more halogen, —CN, —OH, —SH, C$_{1-18}$ alkoxy, C$_{1-18}$ alkylthio, C$_{3-18}$ cycloalkyl, aryl, COOH, COOC$_{1-18}$ alkyl, (C$_{1-18}$ alkyl)$_{0-1}$—CO—C$_{1-18}$ alkyl or SO$_3$H; or the R$^1$ groups together may form a ring; and Ar is aryl that is substituted by one or more electron withdrawing groups. Suitable electron withdrawing groups include —COOH, —COOR$^2$, —SO$_3$R$^2$, —CN, —CO—C$_{1-18}$ alkyl and —C(O)H groups. Preferably, the aryl group is substituted by one or more carboxylic acid, carboxylic acid ester, ketone, aldehyde, sulfonic acid, sulfonate, or nitrile groups.

A preferred group of aryl alkyl polyethers has the following structural formula:

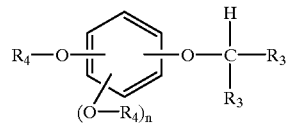

wherein n=1–3 each R$_3$ is independently H or C$_{1-18}$ alkyl that is optionally substituted by one or more halogen, —CN, —OH, —SH, C$_{1-18}$ alkoxy, C$_{1-18}$ alkylthio, C$_{3-18}$ cycloalkyl, aryl, substituted aryl, —COOH, —COOC$_{1-18}$ alkyl, —(C$_{1-18}$ alkyl)$_{0-1}$—COH, —(C$_{1-18}$ alkyl)$_{0-1}$—CO—C$_{1-18}$ alkyl, —CO—C$_{1-18}$ alkyl, —C(O)H or —C$_{2-18}$ alkenyl groups or the R$^3$ groups together may form a ring and each R$_4$ can be C$_{1-18}$ alkyl that is optionally substituted by one or more halogen, —CN, —OH, —SH, C$_{1-18}$ alkoxy, C$_{1-18}$ alkylthio, C$_{3-18}$ cycloalkyl, aryl, substituted aryl, —COOH, —COOC$_{1-18}$ alkyl, —(C$_{1-18}$ alkyl)$_{0-1}$—COH, —(C$_{1-18}$ alkyl)$_{0-1}$—CO—C$_{1-18}$ alkyl, —CO—C$_{1-18}$ alkyl, —C(O)H or —C$_{2-18}$ alkenyl groups.

In each of the above formulas the alkyl groups can be straight-chain or branched, and the cycloalkyl group preferably has 3 to 6 ring carbon atoms but may have additional alkyl substitution up to the specified number of carbon atoms. The aryl groups may be carbocyclic or heterocyclic aryl, but are preferably carbocyclic and more preferably phenyl rings.

Preferred donor compounds include 4-dimethylaminobenzoic acid, ethyl 4-dimethylaminobenzoate, 3-dimethylaminobenzoic acid, 4-dimethylaminobenzoin, 4-dimethylaminobenzaldehyde, 4-dimethylaminobenzonitrile and 1,2,4-trimethoxybenzene.

The photoinitiator compounds are provided in an amount effective to initiate or enhance the rate of cure of the resin system. It has been found that the amount of donor that is used can be critical particularly when the donor is an amine. Too much donor can be deleterious to cure properties. Preferably, the sensitizer is present in about 0.05–5.0 weight percent based on resin compounds of the overall composition. More preferably, the sensitizer is present at 0.10–1.0 weight percent. Similarly, the iodonium initiator is preferably present at 0.05–10.0 weight percent, more preferably at 0.10–5.0 weight percent, and most preferably 0.50–3.0 weight percent. Likewise, the donor is preferably present at 0.01–5.0 weight percent, more preferably 0.05–1.0 weight percent, and most preferably 0.05–0.50 weight percent.

The photopolymerizable compositions of the invention are prepared by simply admixing, under "safe light" conditions, the components of the inventive compositions. Suitable inert solvents may be employed if desired when effecting this mixture. Any solvent may be used which does not react appreciably with the components of the inventive compositions. Examples of suitable solvents include acetone, dichloromethane, and acetonitrile. A liquid material to be polymerized may be used as a solvent for another liquid or solid material to be polymerized. Solventless compositions can be prepared by simply dissolving the aromatic iodonium complex salt and sensitizer in the epoxy resin polyol mixture with or without the use of mild heating to facilitate dissolution.

The compositions of the present invention provide a very useful combination of cure speed, cure depth and shelf life. They cure well even when loaded with large amounts of fillers, and can be used in a variety of applications including graphic arts imaging (e.g. for color proofing systems, curable inks, or silverless imaging), printing plates (e.g. projection plates or laser plates), photoresists, solder masks, electronic conformal coatings, coated abrasives, magnetic media, photocurable adhesives (e.g. for orthodontics) and photocurable composites (e.g., for autobody repair or dentistry).

The photopolymerizable compositions of the invention are prepared by simply admixing, under "safe light" conditions, the components of the inventive compositions. Suitable inert solvents may be employed if desired when effecting this mixture. Any solvent may be used which does not react appreciably with the components of the inventive compositions. Examples of suitable solvents include acetone, dichloromethane, and acetonitrile. A liquid material to be polymerized may be used as a solvent for another liquid or solid material to be polymerized. Solventless compositions can be prepared by simply dissolving the aromatic iodonium complex salt and sensitizer in the epoxy resin with or without the use of mild heating to facilitate dissolution.

Dental applications particularly benefit from the unique compositions of the present invention. Until now, acrylate and methacrylate chemistry has been used extensively for adhesive and restorative dental compositions. This chemistry has the advantage of being curable with visible light using photoinitiator systems, but has the disadvantage of undergoing a relatively high degree of shrinkage during the polymerization process. In contrast, during polymerization the epoxy resins found in the compositions of the present invention shrink significantly less than the acrylate and methacrylate resins of the prior art. The present invention provides a system for curing epoxy resins in an acceptable time frame and to a sufficient depth using visible light source equipment already available in the dental office.

The dental materials may be filled or unfilled and include dental materials such as direct esthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein refers to a filled dental material. The term "restorative" as used herein refers to a composite which is polymerized after it is disposed adjacent to a tooth. The term "prosthesis" as used herein refers to a composite which is shaped and polymerized for its final use (e.g., as crown, bridge, veneer, inlay, onlay or the like) before it is disposed adjacent to a tooth. The term "sealant" as used herein refers to a lightly filled composite or to an unfilled dental material which is cured after it is disposed adjacent to a tooth. "Polymerizable" refers to curing or hardening the dental material, e.g., by free-radical, cationic or mixed reaction mechanisms.

In certain applications, the use of a filler may be appropriate. The choice of filler affects important properties of the composite such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. Epoxy resin compositions of the invention, either alone or in admixture with diluent monomer, can be prepared with refractive indices which approach or approximate the refractive indices of fillers such as quartz (refractive index 1.55), submicron silica (refractive index 1.46), and 5.5:1 mole ratio SiO:ZrO, non-vitreous microparticles (refractive index 1.54). In this way the appearance of the dental material can, if desired, be made to closely approximate the appearance of natural dentition.

Radiopacity is a measurement of the ability of the composite to be detected by x-ray examination. Frequently a radiopaque composite will be desirable, for instance, to enable the dentist to determine whether or not a dental restoration remains sound. Under other circumstances a non-radiopaque composite may be desirable.

The amount of filler which is incorporated into the composite, referred to herein as the "loading level" and expressed as a weight percent based on the total weight of the dental material, will vary depending on the type of filler, the epoxy resin and other components of the composition, and the end use of the composite.

For some dental materials, such as sealants, the epoxy resin compositions of the invention can be lightly filled (e.g., having a loading level of less than about 40 weight percent) or unfilled. Preferably the viscosity of the dental material is sufficiently low to allow its penetration into pits and fissures of occlusal tooth surfaces as well as into etched areas of enamel, thereby aiding in the retention of the dental material. In applications where high strength or durability are desired (e.g., anterior or posterior restoratives, prostheses, crown and bridge cements, artificial crowns, artificial teeth and dentures) the loading level can be as high as about 95 weight percent. For most dental restorative and prosthetic applications a loading level of between about 70 and 90 weight percent is generally preferred.

Fillers may be selected from one or more of any material suitable for incorporation in compositions used for medical applications, such as fillers currently used in dental restorative compositions and the like. The filler is finely divided and preferably has a maximum particle diameter of less than about 50 micrometers and an average particle diameter of less than about 10 micrometers.

The filler can have a unimodal or polymodal (e.g., bimodal) particle size distribution. The filler can be an inorganic material. It can also be a crosslinked organic material that is insoluble in the polymerizable resin, and is optionally filled with inorganic filter. The filler should in any event be non-toxic and suitable for use in the mouth. The filler can be radiopaque, radiolucent or nonradiopaque.

Examples of suitable inorganic fillers are naturally-occurring or synthetic materials such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.). Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169. Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials. Fluoroaluminosilicate glass fillers, either untreated or silanol treated, are particularly preferred. These glass fillers have the added benefit of releasing fluoride at the site of dental work when placed in the oral environment.

Optionally, the surface of the filler particles may be treated with a surface treatment such as a coupling agent in order to enhance the bond between the filler and the polymerizable resin. The coupling agent may be functionalized with reactive curing groups, such as acrylates, methacrylates, epoxies, and the like.

Examples of coupling agents include silanes such as gamma-methacryloxypropyl-trimethoxysilane, gamma-mercaptopropyltriethoxysilane, beta-(3,4-epoxycyclohexyl) ethyltrimethoxysilane, gamma-glycidoxypropyltrimethoxysilane, and the like.

The materials of the present invention can also contain suitable adjuvants such as accelerators, inhibitors, absorbers, stabilizers, pigments, dyes, viscosity modifiers, surface tension depressants and wetting aids, antioxidants, and other ingredients well known to those skilled in the art.

The amounts and types of each ingredient in the dental material should be adjusted to provide the desired physical and handling properties before and after cure. For example, the cure rate, cure stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

When the dental material is applied to a tooth, the tooth can optionally be pre-treated with a primer such as dentin or enamel adhesive by methods known to those skilled in the art.

The invention is further described by reference to the following examples, which are understood to be merely illustrative and not limiting the invention in any way.

EXAMPLE 1

A stock solution of an epoxy resin material was prepared by combining 0.50 g camphorquinone, 1.50 g diphenyliodoniumhexafluoroantimonate (DPI $SbF_6$) and 98.00 g UVR 6105 cycloaliphatic diepoxide, and stirring until homogeneous in the absence of light. UVR 6105 is a cycloaliphatic diepoxide having the following formula:

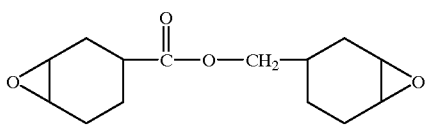

A stock solution of an epoxy resin/acrylate material was prepared by transferring 0.50 g camphorquinone and 1.50 g DPI SbF$_6$ to a glass jar followed by the addition of approximately 0.20 gram of dichloromethane solvent, 88.2 grams of UVR 6105 and 9.80 grams of Ebecryl 1830 polyester hexacrylate from Radcure Specialties. The mixture was stirred until homogeneous in the absence of light.

A variety of donor compounds were evaluated for their photoinduced potential. To evaluate the photoinduced potential of the compounds, a stock initiator solution was prepared by transferring 0.50 grams camphorquinone and 3.00 grams of DPI SbF$_6$ to a 250 ml polyethylene screw-top bottle. Two hundred grams of 99.5+% 2-butanone were transferred to the polyethylene bottle and the contents mixed until homogeneous. The resulting solution contained approximately $2.9 \times 10^{-5}$ moles DPISbF6/gram of stock initiator solution and $1.5 \times 10^{-5}$ moles CPQ/gram of SL 1. The electron donor additives were evaluated at a concentration of $2.9 \times 10^{-5}$ moles donor/gram of SL1. Samples were prepared by transferring $1.16 \times 10^{-4}$ moles of donor to a 13 ml glass vial followed by the addition of 4.0 grams of the stock initiator solution. Vials were capped and vigorously shaken until homogeneous. Samples were then evaluated for relative potential according to the following procedure:

A semi-micro combination pH electrode (Corning model 476540) was connected to a pH meter with millivolt capability (Beckman Φ PIN 123133). The stock initiator solution was used as the millivolt standard in this evaluation. Four grams of the stock initiator solution were transferred to a 13 ml glass vial along with a micro-magnetic stir bar. The sample was placed above a magnetic stirrer which initiated slow stirring of the sample. The electrode was rinsed with water followed by ethanol and then thoroughly dried with a paper towel. The electrode was immersed in the stock initiator solution and the millivolt reading calibrated to read 0.00 mV. The electrode was removed and the sample was irradiated with a Visilux dental curing light having an intensity of about 200 mW/cm$^2$ at a wavelength of 400 to 500 nm for 10 seconds by placing the tip of the light guide directly flush with the center bottom of the vial. Following irradiation the sample was capped and mixed thoroughly by shaking for about 5 seconds. The electrode was rinsed, cleaned thoroughly with ethanol, blotted dry and immersed in the irradiated solution. The millivolts relative to the control was established by pressing the mV button on the pH meter until a stable reading was obtained. The above procedure was repeated with the various donor solutions. The electrode was calibrated with unirradiated stock initiator solution before each run as described previously.

The donor compounds were evaluated for their effect on cure speed of two stock resin solutions. Approximately one gram samples were prepared by transferring $2.9 \times 10^{-5}$ moles of each prospective donor to 1 dram glass vials followed by 1 drop of dichloromethane solvent and 1.0 grams of the stock epoxy resin or epoxy resin/acrylate material. The ingredients were mixed until homogeneous. Each sample was examined for gel time by transferring the solution to a 6mm diameter and 2.5 mm thick Teflon mold with a polyester film clamped in direct contact with the bottom face. The sample was placed directly beneath the light guide of a Visilux 2 dental curing light at a distance of 10 mm for the epoxy samples or 30 mm for the epoxy/acrylate samples. Samples were irradiated up to a maximum of 120 seconds and probed to establish hard gel times. Results are reported in Table 1. Throughout the examples, "NC" means that the material did not cure and "NT" means that the material was not tested.

TABLE 1

| Sample Number | Donor Compound | gms donor/gm resin | gel time epoxy (sec) | gel time epoxy/acrylate (sec) | mV (intial) MEK | mV (photo) MEK |
|---|---|---|---|---|---|---|
| Comparative 1 | none | none | NC | NC | 0 | −25 |
| 2 | 4-dimethyl-amino-benzoic acid | 0.0047 | 14 | 12 | −11 | 184 |
| 3 | ethyl 4-dimethyl-amino-benzoate | 0.0053 | 15 | 13 | −12 | 200 |
| 4 | 3-dimethyl-amino-benzoic acid | 0.0047 | 23 | 20 | −5 | 115 |
| 6 | 1,2,4-trimethoxy-benzene | 0.0053 | 35 | 25 | −3 | 233 |
| 7 | 4-dimethyl-amino-benzoin | 0.0068 | 30 | 29 | −13.4 | 261 |
| 8 | N-phenyl-glycine | 0.0044 | 45 | 35 | −16.4 | 161 |
| 9 | 4-dimethyl-amino-benzonitrile | 0.0045 | 60 | 60 | 9.7 | 266 |
| 10 | 4-dimethyl-amino-benzaldehyde | 0.0043 | 75 | 60 | 8 | 245 |
| Comparative 11 | 4-dimethyl-amino-phenethanol | 0.0046 | NC | 3 hrs | −83.2 | 17 |
| Comparative 12 | dimethyl-aniline | 0.0043 | <12 hrs | 3 hrs | −55 | 54 |
| Comparative 13 | 2,5-di-methoxy-benzyl-alcohol | 0.0049 | <12 hrs | 3 hrs | 30.8 | 52 |
| Comparative 14 | tetrahydro-furfural alcohol | 0.0030 | <12 hrs | NC | −34 | −10 |
| Comparative 15 | 1,2,3-tri-methoxy-benzene | 0.0050 | NC | 3 hrs | −1.9 | 5 |
| Comparative 16 | 1,3,5-tri-methoxy-benzene | 0.0050 | NC | 3 hrs | 10.1 | 28 |
| Comparative 17 | benzyl-alcohol | 0.0031 | <12 hrs | 3 hrs | −13.7 | 24 |
| Comparative 18 | 4-(dimethyl-amino-phenyl-acetic acid | 0.0052 | <12 hrs | NT | −93.5 | −15 |
| Comparative 19 | ethyl 2-di-methyl-amino-benzoate | 0.0047 | <12 hrs | NT | −78 | 19 |
| Comparative 20 | pentamethyl-aniline | 0.0050 | NC | NT | 10 | 71.3 |
| Comparative 21 | N,N-di-methyl-benzyl-amine | 0.0040 | NC | NC | −189.7 | −170 |
| Comparative 22 | trieth-anol- | 0.0042 | NC | NC | −171 | −162 |

TABLE 1-continued

| Sample Number | Donor Compound | gms donor/ gm resin | gel time epoxy (sec) | gel time epoxy/ acrylate (sec) | mV (intial) MEK | mV (photo) MEK |
|---|---|---|---|---|---|---|
| Comparative 23 | amine dihydroxethyl-p-toluidine | 0.0058 | NC | NC | −180 | −98 |
| Comparative 24 | N(2,4-dimethylphenylN, N(bis-2-hydroxyethylamine) | 0.0059 | NC | NC | −90.2 | −42 |

The data illustrates that a variety of donor compounds selected from aromatic ethers or alkyl, aryl amino compounds wherein the aryl group has one or more electron withdrawing substituents including: carboxylic acids and esters, ketones, aldehydes, sulfonic acids and esters, nitriles and halogens serve as effective coinitiators for enhancing the cure speed of epoxy materials in the presence of the visible light sensitizer CPQ and $DPISbF_6$.

EXAMPLE 2

The effect of an aromatic amine donor on the photopolymerization of a cycloaliphatic epoxide was evaluated. Two compositions were prepared as follows:

| Composition A | |
|---|---|
| UVR 6105 | 10.00 g |
| DPI $SbF_6$ | 0.15 g |
| Camphorquinone | 0.05 g |
| Total | 10.20 g |
| Composition B | |
| UVR 6105 | 10.00 g |
| DPI $SbF_6$ | 0.15 g |
| Camphorquinone | 0.05 g |
| Ethyl 4-dimethylaminobenzoate | 0.025 g |
| Total | 10.225 g |

Each composition was prepared by combining the ingredients at room temperature and stirring until homogeneous. A drop of each composition was placed on a polyester film and irradiated with light at 400–500 nm from a Visilux light source from a distance of about 5 mm for a maximum of 60 seconds or until a tack-free material was obtained. Composition A did not cure after a 60 second exposure; Composition B was cured to a hard solid after a 15 second exposure. The composition with the electron donor EDMAB exhibited a rapid photopolymerization, whereas the composition without EDMAB failed to polymerize.

EXAMPLE 3

The effect of various diphenyl iodonium salts was evaluated in epoxy resin compositions with and without the presence of an aromatic amine. Three epoxy containing compositions were prepared as follows:

| Composition A(1) | |
|---|---|
| UVR 6105 | 9.80 g |
| Camphorquinone | 0.05 g |
| DPI $SbF_6$ | 0.15 g |
| Total | 10.00 g |
| Composition B(1) | |
| UVR 6105 | 9.83 g |
| Camphorquinone | 0.05 g |
| DPI $PF_6$ | 0.12 g |
| Total | 10.00 g |
| Composition C(1) | |
| UVR 6105 | 9.86 g |
| Camphorquinone | 0.05 g |
| DPI Cl | 0.091 g |
| Total | 10.00 g |

Ethyl-p-dimethylamino benzoate was added to approximately 5 g aliquots of the above compositions:

| Composition A(2) | |
|---|---|
| Composition A(1) | 4.972 g |
| Ethyl 4-dimethylaminobenzoate | 0.028 g |
| Total | 5.000 g |
| Composition B(2) | |
| Composition B(1) | 4.972 g |
| Ethyl 4-dimethylaminobenzoate | 0.028 g |
| Total | 5.000 g |
| Composition C(2) | |
| Composition C(1) | 4.972 g |
| Ethyl 4-dimethylaminobenzoate | 0.028 g |
| Total | 5.000 g |

Each of the above compositions was prepared by combining the ingredients at room temperature and stirring until homogeneous. Each composition was evaluated for cure speed by irradiation of a 2 mm thick sample with light at a wavelength of 400–500 nm from a Visilux 2 light source at a distance of 10 mm.

Irradiation continued for 120s or until a soft or hard gel was formed. Results are reported in Table 2.

| Composition | Result |
|---|---|
| A(1) | NC |
| B(1) | NC |
| C(1) | NC |
| A(2) | 16 seconds, hard solid |
| B(2) | 19 seconds, soft solid |
| C(2) | NC |

The data illustrates that an epoxy composition can be rapidly photopolymerized when the amine donor EDMAB is used in combination with an iodonium salt with a $PF_6$ or $SbF_6$ counterion. No curing was observed when DPI Cl was used with or without EDMAB.

EXAMPLE 4

The experiment of Example 3 was repeated using an epoxy/acrylate resin in place of the epoxy resin. The epoxy/acrylate resin was prepared by combining 45.00 g UVR 6105 and 5.00 g Ebecryl 1830 at room temperature and stirring until homogeneous. Three epoxy/acrylate containing compositions were prepared as follows:

| Composition D(1) | |
|---|---|
| Epoxy/acrylate | 9.80 g |
| Camphorquinone | 0.05 g |
| DPI SbF$_6$ | 0.15 g |
| Total | 10.00 g |

| Composition E(1) | |
|---|---|
| Epoxy/acrylate | 9.83 g |
| Camphorquinone | 0.05 g |
| DPI PF$_6$ | 0.12 g |
| Total | 10.00 g |

| Composition F(1) | |
|---|---|
| Epoxy/acrylate | 9.86 g |
| Camphorquinone | 0.05 g |
| DPI Cl | 0.09 g |
| Total | 10.00 g |

Ethyl 4-dimethylaminobenzoate was added to approximately 5 g aliquots of the above compositions:

| Composition D(2) | |
|---|---|
| Composition D(1) | 4.972 g |
| Ethyl 4-dimethylaminobenzoate | 0.028 g |
| Total | 5.000 g |

| Composition E(2) | |
|---|---|
| Composition B(1) | 4.972 g |
| Ethyl 4-dimethylaminobenzoate | 0.028 g |
| Total | 5.000 g |

| Composition F(2) | |
|---|---|
| Composition F(1) | 4.972 g |
| Ethyl 4-dimethylaminobenzoate | 0.028 g |
| Total | 5.000 g |

The irradiation time required for formation of a soft gel and/or a hard solid is reported in Table 3.

TABLE 3

| Composition | Time to soft gel | Time to hard solid |
|---|---|---|
| D(1) | 20 seconds (tacky) | NC |
| B(1) | 35 seconds (tacky) | NC |
| F(1) | 45 seconds (tacky) | NC |
| D(2) | 5 seconds (tacky) | 12 seconds |
| E(2) | 8 seconds (tacky) | 25 seconds |
| F(2) | 8 seconds (tacky) | NC |

The data shows that all of the materials initially exhibit a photopolymerization to form a soft, tacky gel indicative of a free radical methacrylate polymerization. Addition of the electron donor EDMAB results in additional cationic curing to a hard solid for compositions with DPI SbF$_6$ and DPI PF$_6$. Compositions with DPI Cl failed to cure to a hard solid with and without EDMAB.

EXAMPLE 5

The effect of varying the concentration of an amine donor compound in the photoinitiator system of the invention was investigated. A stock solution was prepared as follows:

| Stock Solution A | |
|---|---|
| UVR 6105 | 24.50 g |
| DPI SbF$_6$ | 0.375 g |
| Camphorquinone | 0.125 g |
| CH$_2$Cl$_2$ | 0.500 |
| Total | 25.500 g |

The CH$_2$Cl$_2$ was added to solubilize the catalyst. A second stock solution containing the aromatic amine EDMAB was prepared as follows:

| Stock Solution B | |
|---|---|
| UVR 6105 | 23.940 g |
| DPI SbF$_6$ | 0.375 g |
| Camphorquinone | 0.125 g |
| Ethyl 4-dimethylaminobenzoate | 0.560 g |
| CH$_2$Cl$_2$ | 0.500 |
| Total | 25.500 g |

Again, the CH$_2$Cl$_2$ was added to solubilize the catalyst. Sample solutions were prepared by varying the relative proportions of Stock Solution A and Stock Solution B in a 1 g sample. Each solution contained $2.9 \times 10^{-5}$ moles of DPI SbF$_6$. A 2 mm thick sample of each solution was irradiated with a Visilux light source at a distance of about 10 mm until a gel was obtained or for a maximum of 120 seconds. Samples were irradiated 30 minutes after mixing. Results are reported in Table 4, which show the importance of controlling the concentration of the amine donor in initiator systems of the invention.

TABLE 4

| Sample Number | Grams Stock Solution A | Grams Stock Solution B | Mole Ratio Amine:onium Salt | Gel Time (seconds) |
|---|---|---|---|---|
| 1 | 1.0 | 0 | 0 | NC |
| 2 | 1.01 | 0.028 | 0.11 | 100 (surface skin) |
| 3 | 0.96 | 0.07 | 0.29 | 22 |
| 4 | 0.9 | 0.1 | 0.41 | 21 |
| 5 | 0.8 | 0.2 | 0.83 | 22 |
| 6 | 0.7 | 0.3 | 1.20 | 24 |
| 7 | 0.6 | 0.4 | 1.59 | 17 |
| 8 | 0.5 | 0.5 | 2.00 | 26 |
| 9 | 0.4 | 0.6 | 2.40 | 30 |
| 10 | 0.3 | 0.7 | 2.80 | 32 |
| 11 | 0.2 | 0.8 | 3.20 | — |
| 12 | 0.1 | 0.9 | 3.60 | 38 |
| 13 | 0 | 1.0 | 4.0 | 90 (tacky gel) |

EXAMPLE 6

The effect of varying the concentration of an aromatic polyether donor compound in the initiator systems of the invention was investigated. Two stock solutions were prepared, one containing 1,2,4-trimethoxybenzene (TMB) as the donor and one that contained no donor:

| Stock Solution A | | |
| --- | --- | --- |
| UVR 6105 | 98.00% | 9.80 gm |
| DPI SbF$_6$ | 1.50% | 0.15 gm |
| CPQ | 0.50% | 0.05 gm |
| Total | 100.00% | 10.0 gm |
| Stock Solution B | | |
| UVR 6105 | 93.00 | 9.30 gm |
| DPI SbF$_6$ | 1.50% | 0.15 gm |
| TMB | 5.00% | 0.50 gm |
| CPQ | 0.50% | 0.05 gm |
| Total | 100.00% | 10.00 gm |

The solutions were combined in varying proportions to obtain sample solutions having various concentrations of the TMB donor. A 2 mm thick sample of each sample solution was irradiated at a distance of 10 mm using a Visilux 2 light source. The gel times are reported in Table 5.

TABLE 5

| Sample No. | Grams Stock Solution A | Grams Stock Solution B | Molar Equivalents of TMB | Gel Time (seconds) |
| --- | --- | --- | --- | --- |
| 1 | 1.0 | 0 | 0 | NC |
| 2 | 0.975 | 0.026 | 0.26 | 55 |
| 3 | 0.95 | 0.058 | 0.0588 | 38 |
| 4 | 0.90 | 0.10 | 1.0 | 29 |
| 5 | 0.86 | 0.14 | 1.4 | 28 |
| 6 | 0.80 | 0.20 | 2.0 | 27 |
| 7 | 0.70 | 0.30 | 3.0 | 30 |
| 8 | 0.60 | 0.40 | 4.0 | 30 |
| 9 | 0.50 | 0.50 | 5.0 | 30 |
| 10 | 0.40 | 0.60 | 6.0 | NT |
| 11 | 0.30 | 0.70 | 7.0 | 33 |
| 12 | 0.10 | 0.90 | 9.0 | 34 |
| 13 | 0.00 | 1.00 | 10.00 | 38 |

The data illustrates that the addition of various amounts of the aromatic ether TMB results in the photopolymerization of an epoxy composition.

EXAMPLE 7 (PREPARATIVE EXAMPLE)

A filler composition was prepared as follows: 200.3 grams of deionized water was weighed into a 1000 ml rigid poly beaker and adjusted to a pH of 3.02 with trifluoroacetic acid (Aldrich Chem. Co., Milwaukee, Wis.). 9.9099 grams of 3-glycidoxypropyltrimethoxysilane (United Chemical Technologies, Inc., Bristol, Pa.) was slowly added to the water while stirring with a magnetic teflon coated stirring rod. About 50 ml of denatured ethanol was used to rinse the silane addition beaker, and then added to the hydrolyzing aqueous silane solution. The solution was allowed to stir for about 65 minutes at room temperature to thoroughly hydrolyze the silane. After the 65 minutes hydrolysis time 200 grams of a 90/10 weight blend of ball mill ground mined quartz, average particle size 2.25–3.15 microns (3M Co., Maplewood, Minn., PMC-41-5300-0422-9) and a commercially available fumed silica, Aerosil OX-50 (Degussa Inc., Frankfurt, GE) was slowly added to the silane treatment solution. The resulting slurry was stirred for 27 hours at room temperature. The slurry was then divided evenly among three 1000 ml poly beakers and each beaker placed in a convection drying oven for 12 hours at 60° C. The dried cake from each beaker was recombined, mortar and pestled, and then screen in a sealed container on a shaker through a 74 micron nylon screen. The screened powder was then placed in a one pint jar and dried for a final time for 2 hours at 80° C. After a short cool down the jar was then sealed with a metal cap with foil lined paper seal to reduce the moisture vapor transmission into or out of the jar.

EXAMPLE 8

This Example describes the preparation of epoxy resin-based composite materials containing an iodonium salt, an alpha-diketone and an optional amine electron donor.

Two compositions were prepared as follows:

| Composition A | |
| --- | --- |
| UVR 6105 | 10.00 g |
| DPI SbF$_6$ | 0.15 g |
| Camphorquinone | 0.05 g |
| Total | 10.20 g |
| Composition B | |
| UVR 6105 | 10.00 g |
| DPI SbF$_6$ | 0.15 g |
| Camphorquinone | 0.05 g |
| ethyl-p-dimethylaminobenzoate | 0.05 g |
| Total | 10.20 g |

Each composition was prepared by combining the ingredients at room temperature and stirring until homogeneous.

Two composite materials were further prepared by combining 7.50 grams of the filler from Example 7 with 2.50 grams of Compositions A and B respectively. Samples were spatulated until a thick homogeneous paste was obtained.

| Composite A | |
| --- | --- |
| Composition A | 2.50 g |
| Filler from Example 7 | 7.50 g |
| Total | 10.00 g |
| Composite B | |
| Composition B | 2.50 g |
| Filler from Example 7 | 7.50 g |
| Total | 10.00 g |

Samples were evaluated for photopolymerization by determining the hardness of a 2mm thick sample according to the following procedure. A 2 mm thick Teflon block which had a cylindrical hole measuring about 6 mm in diameter extending through the thickness of the block was placed on a film of transparent polyethylene terephthalate (PET) such that one end of the open cylindrical hole of the die was covered by the PET film. The Teflon die was filled with the sample and another film of PET placed on top of the die covering the sample. Hand pressure was applied to the PET film to provide an approximately 2mm thick sample. Samples were irradiated with a Visilux 2 light source for 30 seconds by placing the light wand directly on the PET film which covered the sample at the top of the die. Three sets of samples were prepared in triplicate and stored at 25° C. for 5 minutes, 20 minutes and 24 hours and at 37° C. for 20 minutes and 24 hours respectively. After storage, the PET films were removed and the hardness of the top and bottom of the die was measured using a Barber-Coleman Impressor (a hand-held portable hardness tester; Model GYZJ 934-1; from Barber Coleman Company Industrial Instruments Division, Lovas Park, Ind.) equipped with an indenter. For each sample tested, three readings were taken at the top and bottom of each sample. The readings were averaged for each composition and storage condition. A hardness value of zero indicated limited or no polymerization. Bottom hardness values significantly less than those of the top indicate limited depth of cure. Results are summarized in Table 6 below.

TABLE 6

| Sample | Side Tested | 25° C. | | | 37° C. | |
|---|---|---|---|---|---|---|
| | | 5 minutes | 20 minutes | 24 hours | 20 minutes | 24 hours |
| Composite A | Top | 0 | 0 | 0 | 0 | 0 |
| | Bottom | 0 | 0 | 0 | 0 | 0 |
| Composite B | Top | 0 | 0 | 64 | 46 | 74 |
| | Bottom | 0 | 0 | 60 | 50 | 72 |

The data shows that composite B, which contains the donor EDMAB, exhibits significant top and bottom polymerization when post-cured for 20 or more minutes at 37° C. or for 24 hrs at 25° C., whereas Composite A without EDMAB fails to exhibit significant polymerization under any of the experimental conditions.

EXAMPLE 9

This Example describes the preparation of epoxymethacrylate resin-based composite materials containing an iodonium salt, an alpha-diketone and an optional amine electron donor.

Two compositions were prepared as follows:

| Composition A | |
|---|---|
| UVR 6105 | 9.00 g |
| Ebecryl 1830 | 1.00 g |
| DPI SbF$_6$ | 0.15 g |
| Camphorquinone | 0.05 g |
| Total | 10.20 g |

| Composition B | |
|---|---|
| UVR 6105 | 9.00 g |
| Ebecryl 1830 | 1.00 g |
| DPI SbF$_6$ | 0.15 g |
| Camphorquinone | 0.05 g |
| ethyl 4-dimethylaminobenzoate | 0.05 g |
| Total | 10.20 g |

Each composition was prepared by combining the ingredients at room temperature and stirring until homogeneous.

Two composite materials were further prepared by combining 7.50 grams of the filler from Example 7 with 2.50 grams of Compositions A and B respectively. Samples were spatulated until a thick homogeneous paste was obtained.

| Composition A | |
|---|---|
| Composition A | 2.50 g |
| Filler from Example 7 | 7.50 g |
| Total | 10.00 g |

| Composition B | |
|---|---|
| Composition B | 2.50 g |
| Filler from Example 7 | 7.50 g |
| Total | 10.00 g |

Samples were evaluated for photopolymerization by determining the hardness of a 2 mm thick sample according to the procedure described in Example 8. Results are summarized in Table 7 below.

TABLE 7

| Sample | Side Tested | 25° C. | | | 37° C. | |
|---|---|---|---|---|---|---|
| | | 5 minutes | 20 minutes | 24 hours | 20 minutes | 24 hours |
| Composite A | Top | 0 | 0 | 0 | 0 | 0 |
| | Bottom | 0 | 0 | 0 | 0 | 0 |
| Composite B | Top | 0 | 0 | 63 | 45 | 68 |
| | Bottom | 0 | 0 | 59 | 38 | 64 |

The data shows that Composite B, which contains the donor EDMAB exhibits significant top and bottom polymerization when post-cured for 20 or more minutes at 37° C. or for 24 hrs at 25° C., whereas Composite A without EDMAB fails to exhibit significant polymerization under any of the experimental conditions.

The above specification, examples and data provide a complete description of the manufacture and use of the composition of the invention. The United States patents referred to in the foregoing specification are incorporated into the specification by reference. Since many embodiments of the invention can be made without departing from the spirit and scope of the invention, the invention resides in the claims hereinafter appended.

We claim:

1. A photopolymerizable composition comprising:
   (a) an epoxy resin and
   (b) a photoinitiator system comprising:
      (i) an iodonium salt;
      (ii) a visible light sensitizer; and
      (iii) an electron donor compound, wherein the photoinitiator system has a photoinduced potential greater than or equal to that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone.

2. The composition of claim 1 wherein the donor compound is described by the following structural formula:

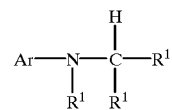

wherein $R^1$ are independently H; $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, COOH, COOC$_{1-18}$ alkyl, (C$_{1-18}$ alkyl)$_{0-1}$—CO—C$_{1-18}$ alkyl, or SO$_3$R$^2$; or aryl that is optionally substituted by one or more electron withdrawing groups; where $R^2$ is H; $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, COOH, $COOC_{1-18}$ alkyl, $(C_{1-18}$ alkyl$)_{0-1}$—CO—$C_{1-18}$ alkyl, or $SO_3H$, or $R^1$ is aryl that is optionally substituted by one or more electron withdrawing groups; or the $R^1$ groups together may form a ring; and Ar is aryl that is substituted by one or more electron withdrawing groups.

3. The composition of claim 2 wherein the aryl group is substituted by one or more carboxylic acid, carboxylic acid ester, ketone, aldehyde, sulfonic acid, sulfonate, or nitrile groups.

4. The composition of claim 2 wherein the aryl group is substituted by one or more moieties selected from the group consisting of —COOH, —$COOC_{1-18}$ alkyl, —$SO_3R^2$, —CN, —CO—$C_{1-18}$ alkyl and —C(O)H groups, where $R^2$ is H, $C_{1-18}$ alkyl that is optionally substituted by one or more halogen, —CN, —OH, —SH, —$C_{1-18}$ alkoxy, $C_{1-18}$ alkylthio, —$C_{3-18}$ cycloalkyl, aryl, —COOH, —$COOC_{1-18}$ alkyl, —$C_{1-18}$ alkyl$)_{0-1}$—CO—$C_{1-18}$ alkyl; —$SO_3H$, —CN or halogen groups, or aryl that is optionally substituted by one or more electron withdrawing groups.

5. The composition of claim 1 wherein the donor compound is selected from the group consisting of 4-dimethylaminobenzoic acid, ethyl 4-dimethylaminobenzoate, 3-dimethylaminobenzoic acid, 4-dimethylaminobenzoin, 4-dimethylaminobenzaldehyde, 4-dimethylaminobenzonitrile and 1,2,4-trimethoxybenzene.

6. The composition of claim 1 wherein the donor compound is an alkyl, aryl polyether.

7. The composition of claim 1 wherein the donor compound is an alkyl, aryl polyether having the structural formula:

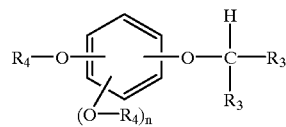

wherein n=1–3 each $R_3$ is independently H or $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, substituted aryl, —COOH, —$COOC_{1-18}$ alkyl, —$(C_{1-18}$ alkyl$)_{0-1}$—COH, —$(C_{1-18}$ alkyl$)_{0-1}$—CO—$C_{1-18}$ alkyl, —CO—$C_{1-18}$ alkyl, —C(O)H or —$C_{2-18}$ alkenyl groups, or the $R^3$ groups together may form a ring and each $R_4$ can be $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, substituted aryl, —COOH, —$COOC_{1-18}$ alkyl, — $(C_{1-18}$ alkyl$)_{0-1}$—COH, —$(C_{1-18}$ alkyl$)_{0-1}$—CO—$C_{1-18}$ alkyl, —CO—$C_{1-18}$ alkyl, —C(O)H or —$C_{2-18}$ alkenyl groups.

8. The composition of claim 1 wherein the iodonium salt is an aryl iodonium salt.

9. The composition of claim 1 wherein the iodonium salt comprises diphenyliodonium chloride, diphenyl iodonium hexafluorophosphate, diphenyl iodonium hexafluoroantimonate, diphenyl iodonium tetrafluoroborate, or a mixture thereof.

10. The composition of claim 1 wherein the sensitizing compound comprises a ketone.

11. The composition of claim 1 wherein the sensitizing compound comprises an alphadiketone.

12. The composition of claim 1 wherein the sensitizing compound comprises a ketocoumarin, aminoarylketone, or a para-substituted aminostyrylketone compound.

13. The composition of claim 1 wherein the sensitizing compound comprises camphorquinone.

14. The composition of claim 1 wherein the composition cures to a tack-free gel within 60 seconds after exposure to visible light.

15. The composition of claim 1 wherein the epoxy resin comprises a cycloaliphatic epoxide or diepoxide.

16. The composition of claim 1 wherein the epoxy resin comprises a bisphenol-A diepoxide.

17. The composition of claim 16 wherein the ethylenically unsaturated compound is an ester of acrylic acid or methacrylic acid.

18. The composition of claim 16 wherein the ethylenically unsaturated compound comprises methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate or a mixture thereof.

19. The composition of claim 1 wherein the epoxy resin contains ethylenic unsaturation.

20. The composition of claim 1 further comprising an ethylenically unsaturated compound.

21. A composition of claim 1, wherein said composition is a graphic arts imaging composition.

22. A composition of claim 1, wherein said composition is selected from the group consisting of photoresist compositions, solder mask compositions, electronic conformal coating compositions, coated abrasive compositions and magnetic media compositions.

23. A photopolymerizable composition comprising:
   (a) an epoxy resin;
   (b) a photoinitiator system comprising:
      (i) a diaryliodonium hexafluoroantimonate or diaryliodonium hexafluorophosphate;
      (ii) camphorquinone and
      (iii) an electron donor described by the following structural formula:

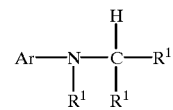

wherein $R^1$ are independently H; $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, COOH, $COOC_{1-18}$ alkyl, $(C_{1-18}$ alkyl$)_{0-1}$—CO—$C_{1-18}$ alkyl, or $SO_3R^2$; or aryl that is optionally substituted by one or more electron withdrawing groups; where $R^2$ is H; $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, COOH, $COOC_{1-18}$ alkyl, $(C_{1-18}$ alkyl$)_{0-1}$—CO—$C_{1-18}$ alkyl, or $SO_3H$, or $R^1$ is aryl that is optionally substituted by one or more electron withdrawing groups; or the $R^1$ groups together may form a ring; and Ar is aryl that is substituted by one or more electron withdrawing groups.

24. A photopolymerizable composition comprising:
   (a) an epoxy resin;
   (b) a photoinitiator system comprising:
      (i) a diaryliodonium hexafluoroantimonate or diaryliodonium hexafluorophosphate;
      (ii) camphorquinone and (iii) an electron donor described by the following structural formula:

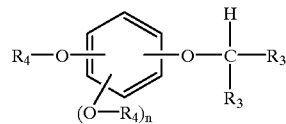

wherein n=1–3 each $R_3$ is independently H or $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, substituted aryl, —COOH, —COOC$_{1-18}$ alkyl, —($C_{1-18}$ alkyl)$_{0-1}$—COH, —($C_{1-18}$ alkyl)$_{0-1}$—CO—$C_{1-18}$ alkyl, —CO—$C_{1-18}$ alkyl, —C(O)H or —$C_{2-18}$ alkenyl groups, or the $R^3$ groups together may form a ring and each $R_4$ can be $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, substituted aryl, —COOH, —COOC$_{1-18}$ alkyl, —($C_{1-18}$ alkyl)$_{0-1}$—COH, —($C_{1-18}$ alkyl)$_{0-1}$—CO—$C_{1-18}$ alkyl, —CO—$C_{1-18}$ alkyl, —C(O)H or —$C_{2-18}$ alkenyl groups.

25. A method for photopolymerization comprising the step of irradiating a photopolymerizable composition with light having a wavelength between about 400 and 1000 nanometers until said composition gels or hardens, said composition comprising:
(a) an epoxy resin;
(b) a photoinitiator system, said photoinitiator system comprising:
   (i) an iodonium salt;
   (ii) a visible light sensitizer; and
   (iii) an electron donor compound, wherein the photoinitiator system has a photoinduced potential of at least about 100 mV relative to a standard solution of $2.9 \times 10^{-5}$ moles per gram diphenyliodonium hexafluoroantimonate and $1.5 \times 10^{-5}$ moles per gram camphorquinone in 2-butanone.

26. The method of claim 25 wherein the composition additionally comprises an ethylenically unsaturated compound.

27. A photopolymerizable dental composition comprising:
(a) an epoxy resin;
(b) a photoinitiator system comprising:
   (i) an iodonium salt;
   (ii) a visible light sensitizer; and
   (iii) an electron donor compound, wherein the photoinitiator system has a photoinduced potential of at least about 100 mV relative to a standard solution of $2.9 \times 10^{-5}$ moles/g diphenyl iodonium hexafluoroantimonate and $1.5 \times 10^{-5}$ moles/g camphorquinone in 2-butanone.

28. A composition of claim 27, wherein said composition is a dental adhesive composition.

29. A composition of claim 27, wherein said composition is a dental composite material composition.

30. A composition of claim 27, wherein said composition is a dental sealant composition.

31. A composition of claim 27, wherein said composition is an orthodontic adhesive composition.

* * * * *

UNITED STATES PATENT AND TRADEMARK OFFICE
CERTIFICATE OF CORRECTION

PATENT NO.: 6,025,406

DATED: February 15, 2000

INVENTOR(S): Joel D. Oxman and Dwight W. Jacobs

It is certified that error appears in the above-identified patent and that said Letters Patent is hereby corrected as shown below:

Claim 2, Column 23, line 4, "SO$_3$H," should read --SO$_3$H;--.

Claim 23, Column 24, line 58, "SO$_3$H," should read --SO$_3$H;--.

Signed and Sealed this

Third Day of April, 2001

*Attest:*

NICHOLAS P. GODICI

*Attesting Officer*  *Acting Director of the United States Patent and Trademark Office*